(12) United States Patent
Roy et al.

(10) Patent No.: US 6,222,307 B1
(45) Date of Patent: Apr. 24, 2001

(54) PLATINUM TIP ECP SENSOR AND FABRICATION THEREOF

(75) Inventors: Prodyot Roy, Saratoga; Donald A. Hale, San Jose, both of CA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/222,991

(22) Filed: Dec. 30, 1998

Related U.S. Application Data
(60) Provisional application No. 60/070,096, filed on Dec. 31, 1997.

(51) Int. Cl.[7] .................................................. H01J 1/00
(52) U.S. Cl. ........................................... 313/326; 313/631
(58) Field of Search .................................... 313/326, 324, 313/325, 335, 348, 350, 352, 353, 354, 355, 356, 631

*Primary Examiner*—Vip Patel
(74) *Attorney, Agent, or Firm*—Nixon & Vanderhye

(57) ABSTRACT

A method for fabricating an electrode having extended operating life comprising brazing a cap and adapter to an insulator composed of magnesium oxide-stabilized zirconia (MSZ), calcium oxide stabilized zirconia (CSZ) or yttroim oxide-stabilized (YSZ). Electrodes comprising insulators composed of CSZ, MSZ and/or YSZ are also described.

13 Claims, 7 Drawing Sheets

PLATINUM TIP ECP SENSOR AND FABRICATION THEREOF

This application claims the benefit of U.S. Provisional Application No. 60/070,096, filed Dec. 31, 1997.

FIELD OF THE INVENTION

The present invention relates to electrodes, especially platinum tip ECP sensors having improved sensor life, and methods for their fabrication.

BACKGROUND OF THE INVENTION

Nuclear reactors are used in central-station electric power generation, research and propulsion. A reactor pressure vessel contains the reactor coolant, i.e. water, which removes heat from the nuclear core. Respective piping circuits carry the heated water or steam to the steam generators or turbines and carry circulated water or feedwater back to the vessel. Operating pressures and temperatures for the reactor pressure vessel are about 7 MPa and 288° C. for a boiling water reactor (BWR), and about 15 MPa and 320° C. for a pressurized water reactor (PWR). The materials used in both BWRs and PWRs must withstand various loading, environmental and radiation conditions.

Some of the materials exposed to high-temperature water include carbon steel, alloy steel, stainless steel, nickel-based, cobalt-based and zirconium-based alloys. Despite careful selection and treatment of these materials for use in water reactors, corrosion occurs in the materials exposed to the high-temperature water. Such corrosion contributes to a variety of problems, e.g., stress corrosion cracking, crevice corrosion erosion corrosion, sticking of pressure relief valves and buildup of the gamma radiation-emitting Co-60 isotope.

Stress corrosion cracking (SCC) is a known phenomenon occurring in reactor components, such as structural members, piping, fasteners and welds exposed to high-temperature water. As used herein, SCC refers to cracking propagated by static or dynamic tensile stressing in combination with corrosion at the crack tip. The reactor components are subject to a variety of stresses associated with, e.g., differences in thermal expansion, the operating pressure needed for the containment of the reactor cooling water, and other sources such as residual stress from welding, cold working and other asymmetric metal treatments. In addition, water chemistry, welding, heat treatment, and radiation can increase the susceptibility of metal in a component to SCC.

It is well known that SCC occurs at higher rates when oxygen is present in the reactor water in concentrations of about 5 ppb (parts per billion) or greater. SCC is further increased in a high radiation flux where oxidizing species, such as oxygen, hydrogen peroxide, and short-lived radicals, are produced from radiolytic decomposition of the reactor water. Such oxidizing species increase the electrochemical corrosion potential (ECP) of metals. Electrochemical corrosion is caused by a flow of electrons from anodic to cathodic areas on metallic surfaces. The ECP is a measure of the thermodynamic tendency for corrosion phenomena to occur, and is a fundamental parameter in determining rates of, e.g., SCC, corrosion fatigue, corrosion film thickening, and general corrosion.

In a BWR, the radiolysis of the primary water coolant in the reactor core causes the net decomposition of a small fraction of the water to the chemical products $H_2$, $H_2O_2$, $O_2$ and oxidizing and reducing radicals. For steady-state operating conditions, equilibrium concentrations of $O_2$, $H_2O_2$, and $H_2$ are established in both the water which is recirculated and the steam going to the turbine. This concentration Of $O_2$, $H_2O_2$, and $H_2$ is oxidizing and results in conditions that can promote intergranular stress corrosion cracking (IGSCC) of susceptible materials of construction. One method employed to mitigate IGSCC of susceptible material is the application of hydrogen water chemistry (HWC), whereby the oxidizing nature of the BWR environment is modified to a more reducing condition. This effect is achieved by adding hydrogen gas to the reactor feedwater. When the hydrogen reaches the reactor vessel, it reacts with the radiolytically formed oxidizing species to reform water, thereby lowering the concentration of dissolved oxidizing species in the water in the vicinity of metal surfaces. The rate of these recombination reactions is dependent on local radiation fields, water flow rates and other variables.

The injected hydrogen reduces the level of oxidizing species in the water, such as dissolved oxygen, and as a result lowers the ECP of metals in the water. However, factors such as variations in water flow rates and the time or intensity of exposure to neutron or gamma radiation result in the production of oxidizing species at different levels in different reactors. Thus, varying amounts of hydrogen have been required to reduce the level of oxidizing species sufficiently to maintain the ECP below a critical potential required for protection from IGSCC in high-temperature water. As used herein, the term "critical potential" means a corrosion potential at or below a range of values of about −0.230 to −0.300 V based on the standard hydrogen electrode (SHE) scale. IGSCC proceeds at an accelerated rate in systems in which the ECP is above the critical potential, and at a substantially lower or zero rate in systems in which the ECP is below the critical potential. Water containing oxidizing species such as oxygen increases the ECP of metals exposed to the water above the critical potential, whereas water with little or no oxidizing species present results in an ECP below the critical potential.

It has been shown that IGSCC of Type 304 stainless steel (composition in weight % 18.0–20.0 Cr, 8.0–10.0 Ni, 2.00 Mn, 1.0 Si, 0.08 C, 0.08 S, 0.045 P) used in BWRs can be mitigated by reducing the ECP of the stainless steel to values below −0.230 V(SHE). An effective method of achieving this objective is to use HWC. However, high hydrogen additions, e.g., of about 200 ppb or greater, that may be required to reduce the ECP below the critical potential, can result in a higher radiation level in the steam-driven turbine section from incorporation of the short-lived N-16 species in the steam. For most BWRs, the amount of hydrogen addition required to provide mitigation of IGSCC of pressure vessel internal components results in an increase in the main steam line radiation monitor by a factor of five. This increase in main steam line radiation can cause high, even unacceptable, environmental dose rates that can require expensive investments in shielding and radiation exposure control. Thus, recent investigations have focused on using minimum levels of hydrogen to achieve the benefits of HWC with minimum increase in the main steam radiation dose rates.

In order to evaluate or predict a material's performance at operating conditions of a reactor, it is important to know the ECP values of the various structured components. Electrochemical potential monitoring is typically carried out employing paired electrochemical half-cell probes or electrodes which are mounted within the recirculation piping and accessed to the external environment through gland-type mountings or the like. Where the electrode system of interest involves a metal-metal ion couple, the reference electrode may conveniently be a metal-metal insoluble salt-anion electrode. A suitable reference electrode may be based, for example, on the half-cell reaction between silver and silver chloride. Calibration of the cell defining electrode pair is carried out by appropriate Nernst-based electrochemical calculations, as well as thermodynamic evaluation in combination with laboratory testing within a simulated environment against a standard electrode.

A reference electrode which is currently employed is a platinum tip reference electrode for monitoring the ECP. According to conventional design, a platinum cap is brazed to a metallized sapphire insulator post using pure silver braze. However, the metallizing process is not consistently reproducible and, in many cases, results in early failure. The silver braze forms an alloy with the platinum cap at high brazing temperature which, in turn, causes delamination of the metallized layer from the sapphire, which is a further reason for early life failure. In addition, it has been observed that the sapphire dissolves or undergoes corrosion more rapidly in high velocity water which causes mid-life failure.

A need exists for an improved electrode structure with enhanced operating life for use in measuring ECP. A particular objective is to increase the sensor life to at least one fuel cycle of the reactor. The present invention seeks to satisfy that need.

SUMMARY OF THE INVENTION

It has been discovered, according to the present invention, that it is possible to extend the operating life of an electrode by employing an alkaline earth metal or rare earth metal-stabilized zirconia ceramic for the insulator. More particularly, the operating life of the electrode may be extended by using a calcia-stabilized zirconia (CaO—$ZrO_2$ hereinafter referred to as CSZ), magnesia-stabilized zirconia (MgO—$ZrO_2$—herein referred to as MSZ) or yttria-stabilized zirconia ($Y_2O_3$—$ZrO_2$—herein referred to as YSZ) ceramic for the insulator. It has been found surprisingly, according to the present invention that the dissolution rate of magnesia-stabilized zirconia, calcia stabilized zirconia or yttria-stabilized zirconia is 10 to 50 times less than that of sapphire.

According to a first aspect, the present invention provides a method of fabricating an electrode including an MSZ, CSZ or YSZ insulator with a cap at one end thereof and an adapter at the other end thereof, comprising brazing the cap and adapter to the MSZ, CSZ or YSZ insulator using an active metal alloy braze. The resulting brazed assembly except the cap may then be masked with a suitable masking material, such as Teflon ® tubing, and the exposed cap is ion implanted according to conventional techniques at an elevated temperature under vacuum with platinum to provide a layer of platinum deposited on the cap. As a further optional step, the cap and adapter are masked with metal foil, and the exposed insulator region is plasma sprayed with a fine powder of MSZ, CSZ or YSZ at elevated temperature, typically in the region of 200–700° C. (deposition temperature) to provide a layer of MSZ, CSZ or YSZ on the sensor and the braze joint.

According to a further aspect, an outer platinum cap (sheath) in a first step is brazed to an electrode cap using a first active braze alloy. The resulting outer platinum cap/ inner cap assembly together with an adapter are then brazed to a MSZ, CSZ or YSZ ceramic insulator using a second lower temperature active metal braze. The active braze alloy used in the first step should have a melting temperature which is higher than the braze used in the second step. As an optional third step, the cap and adapter are masked and the exposed insulator area is plasma sprayed with a fine powder of MSZ, CSZ or YSZ at elevated temperature, typically in the region of 500–700° C. to provide a layer of MSZ, CSZ or YSZ on the sensor and the braze joint.

According to another aspect, the present invention provides an electrode suitable for use within the environment of a reactor core of a nuclear power facility fabricated according to the methods of the invention.

According to a further aspect, there is provided an electrode comprising a housing, a cap and an insulator braze jointed to the cap and housing. The insulator comprises an alloy selected from calcium oxide-stabilized zirconia (CSZ), magnesium oxide-stabilized zirconia (MSZ) and yttrium oxide-stabilized zirconia (YSZ). MSZ, CSZ and YSZ typically have the following compositions: MSZ: $ZrO_2$ with 4–8 wt % MgO; CSZ: $ZrO_2$ with 4–8 wt % CaO; YSZ: $ZrO_2$ with 6–10 wt % $Y_2O_3$. The cap usually comprises an inner cap of alloy 42 and an outer platinum cap. In addition, a coating of MSZ, CSZ or YSZ may be provided over an exterior surface of the insulator which covers the braze joints.

DETAILED DESCRIPTION OF PREFERRED EMBODIMENTS

Figure 1:
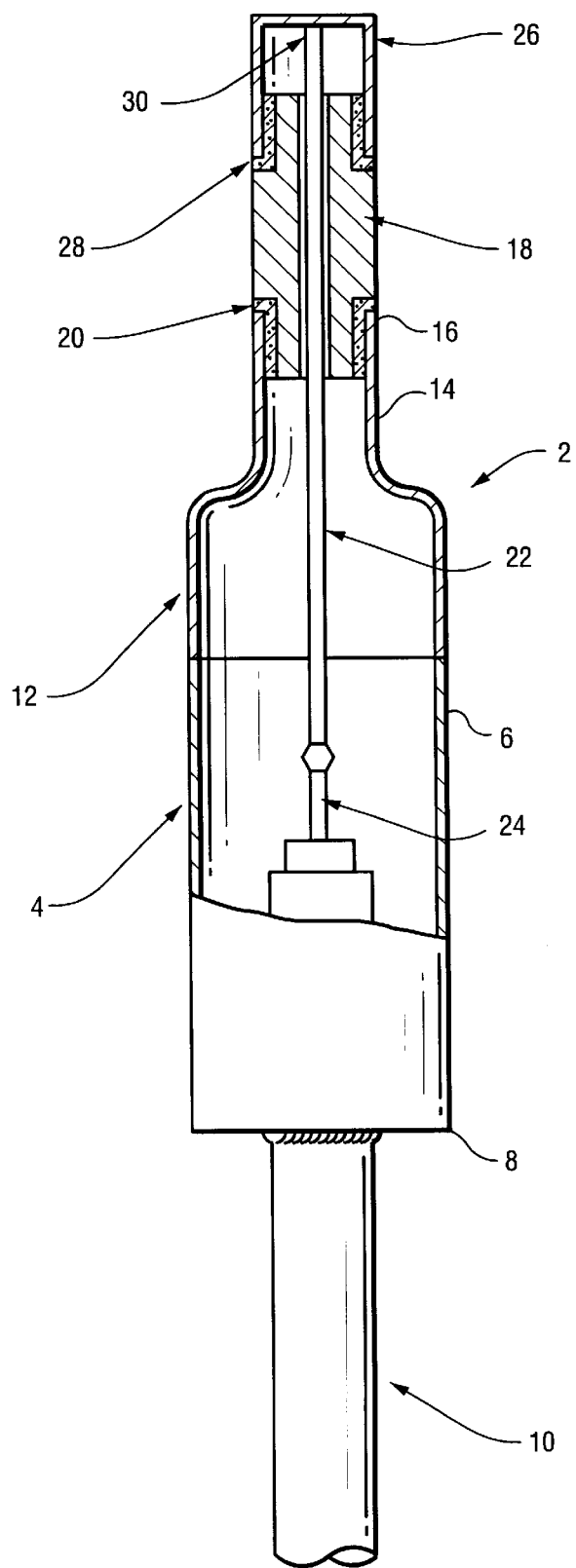
FIG. 1 is a partial cross-section of an electrode showing the location of the ceramic to metal active braze joints.

Referring to FIGS. 1–4, there is shown an electrode, generally referenced 2, having a housing 4 typically of stainless steel, with a first and second ends 6,8. A stainless steel sheathed mineral insulated signal cable 10 is mounted on the second end 8. The first end 6 is connected to adapter 12 fabricated typically of alloy 42 (alloy 42 is a low expansion iron based on alloy with about 42 wt % Ni and about 58 wt % Fe). The adapter 12 has a necked portion 14 which terminates in a mouth 16. An insulator 18 is located in the mouth 16 and is bonded to the mouth by a braze joint 20. The insulator 18 comprises an alloy selected from calcium oxide-stabilized zirconia, magnesium oxide-stabilized zirconia and yttrium oxide-stabilized zirconia. A post wire 22 extends longitudinally through the adapter and housing and is connected to the signal cable at wire connection point 24. The insulator 18 and is brazed to a post cap 26 at braze joint 28. The post cap is typically fabricated from alloy 42 and is ion implanted with platinum. The post wire is brazed to an interior surface of the post cap at braze joint 30.

Figure 2:
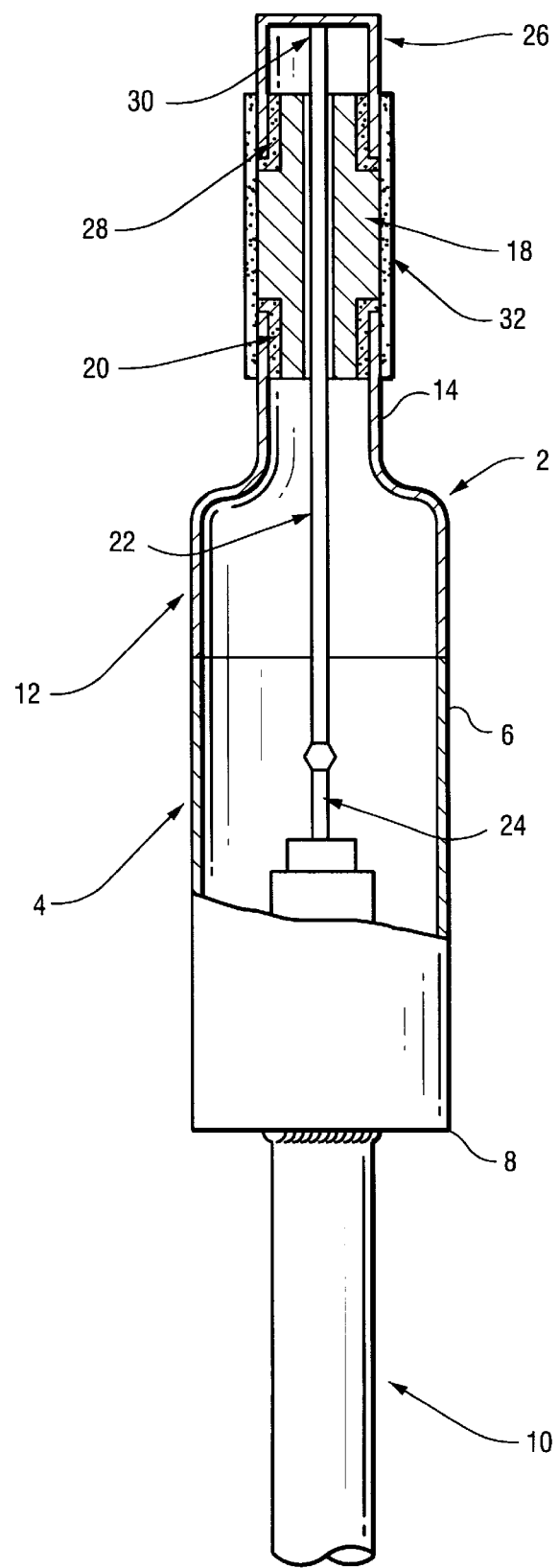
FIG. 2 is a partial cross-section of an electrode showing a plasma spray barrier coat.

In FIG. 2, like numerals refer to like parts as shown in FIG. 1. The electrode in FIG. 2 further includes a plasma spray barrier coat 32 on an exterior surface of the insulator 18 and extending down over the necked portion 14 of the adapter 12.

Figure 3:
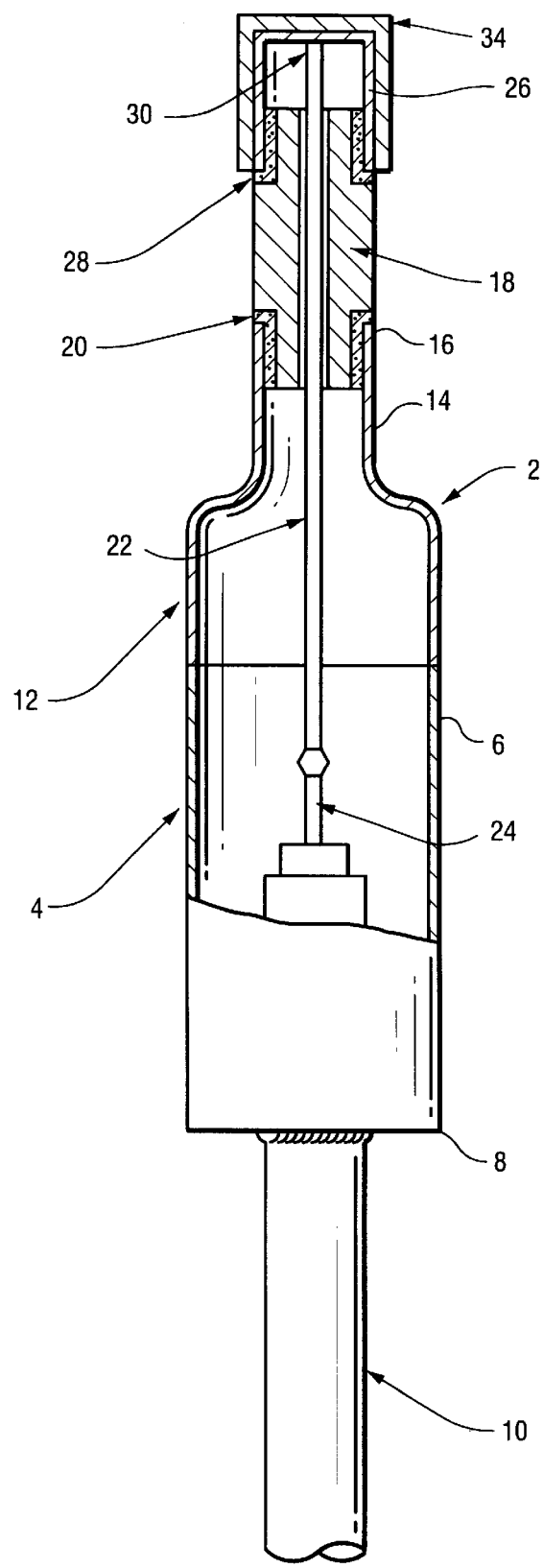
FIG. 3 is a partial cross-section of an electrode including a clad post cap comprising a platinum outer cap brazed to an alloy 42 inner cap.

In FIG. 3, like numerals refer to like parts as shown in FIG. 1. The electrode in FIG. 3 further includes a clad post cap 34 including a platinum outer cap brazed to an alloy 42 inner cap 26.

Figure 4:
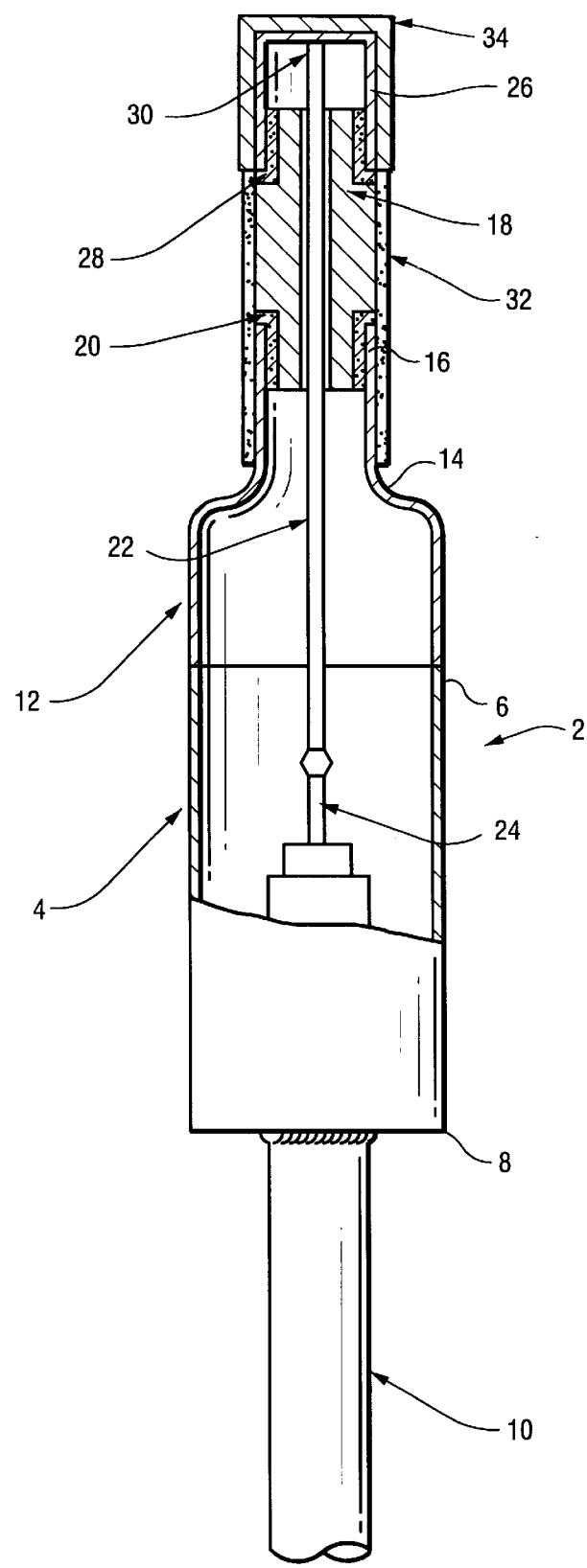
FIG. 4 is a partial cross-section of an electrode including a clad post cap and a plasma spray barrier coat.

In FIG. 4, like numerals refer to like parts as shown in FIG. 1. The electrode in FIG. 4 includes plasma spray barrier coat 32 on an exterior surface of the insulator 18 extending down over the necked portion 14 of the adapter 12, and clad post cap 34 including a platinum outer cap brazed to an alloy 42 inner cap 26.

Figure 5A:
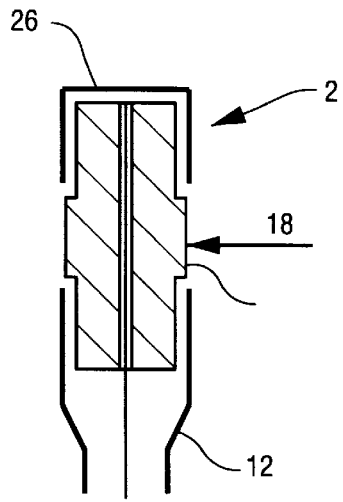
FIGS. 5a–5c is a schematic showing fabrication of an electrode of the invention according to a first method.
Figure 5B:
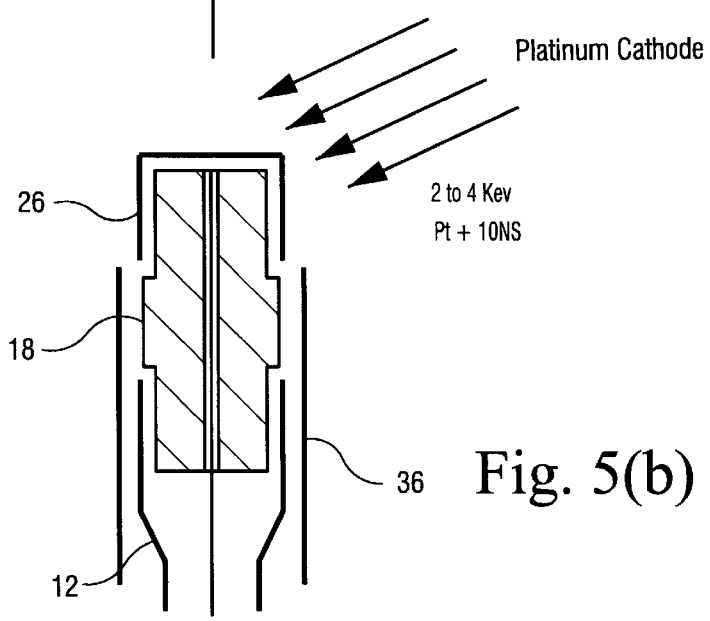
Figure 5C:
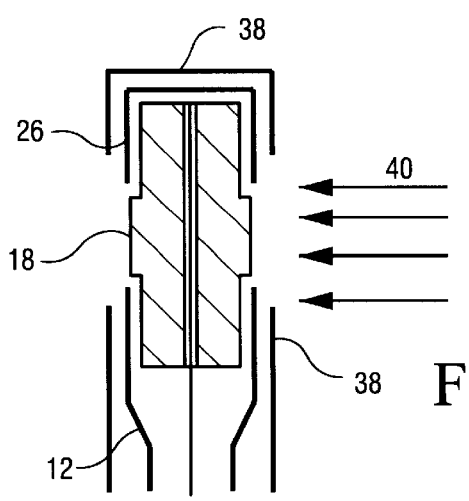

Referring to FIGS. 5(a)–(c), a first method of the invention for fabricating an electrode/sensor 2 comprises brazing, typically in a single step, post cap 26 and adapter 12 to insulator 18 (FIG. 5(a)). The insulator 18 is formed of zirconia ($ZrO_2$) stabilized with magnesium oxide (MgO) (MSZ), calcium oxide (CaO) (CSZ) and/or yttrium oxide ($Y_2O_3$) (YSZ). Typical elemental compositions of these zirconia alloys are set forth below:

MSZ: $ZrO_2$ with 4–8 wt % MgO

CSZ: $ZrO_2$ with 4–8 wt % CaO

YSZ: $ZrO_2$ with 6–10 wt % $Y_2O_3$

The cap and adapter are brazed to the insulator using active metal alloy braze. This braze typically has the following composition:

80–90 wt % Ni; 5–8 wt % Cr; 2–4 wt % B; 3–4 wt % Si (Braze Temperature: 980–1040° C.).

In the second step (FIG. 5(b)), the brazed assembly comprising the adapter and post cap brazed to the ceramic insulator 18 is masked, suitably with 20 mil Teflon® tubing 36. The cap 26 is then ion implanted with platinum under a vacuum at an elevated temperature, typically in the region of 75–100° C. The ion energies employed use the range from 2 to 4 Kev. to a depth of about 100 Angstrom. The ion implantation is continued until a layer of pure platinum is deposited to a thickness in the region of 2,000 to 3,000 Angstrom.

A third step may then be carried out (FIG. 5(c)) in which the post cap 26 and adapter 12 are masked with metal foil 38. The exposed insulator region is then plasma sprayed with a fine powder 40, typically 5–250 microns, more usually 5–125 microns of CSZ, MSZ and/or YSZ at an elevated temperature, typically at about 600–700° C. The average particle temperature during the deposition ranges from about 2500–3300° C., more usually around 2800–3200° C., depending on the particle size (higher temperatures are typically associated with smaller particles).

Figure 6A:
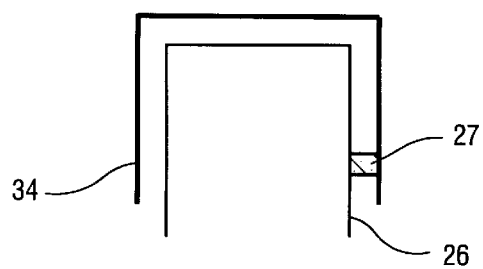
FIGS. 6a–6c is a schematic showing fabrication of an electrode of the invention according to a second method.
Figure 6B:
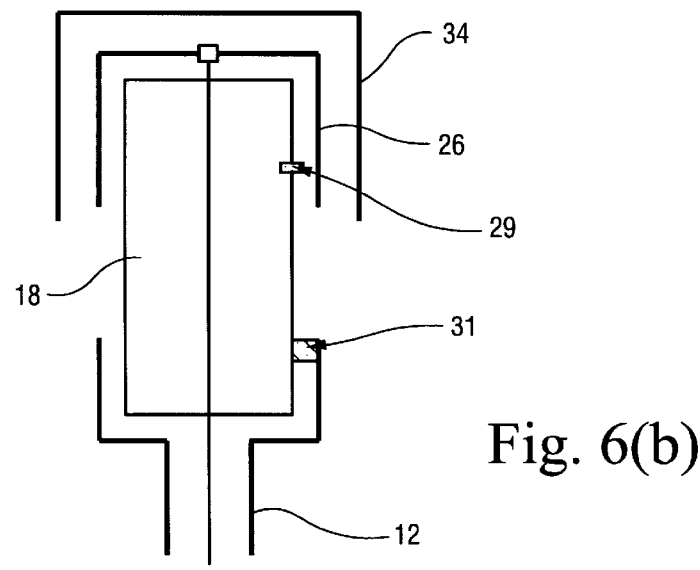
Figure 6C:
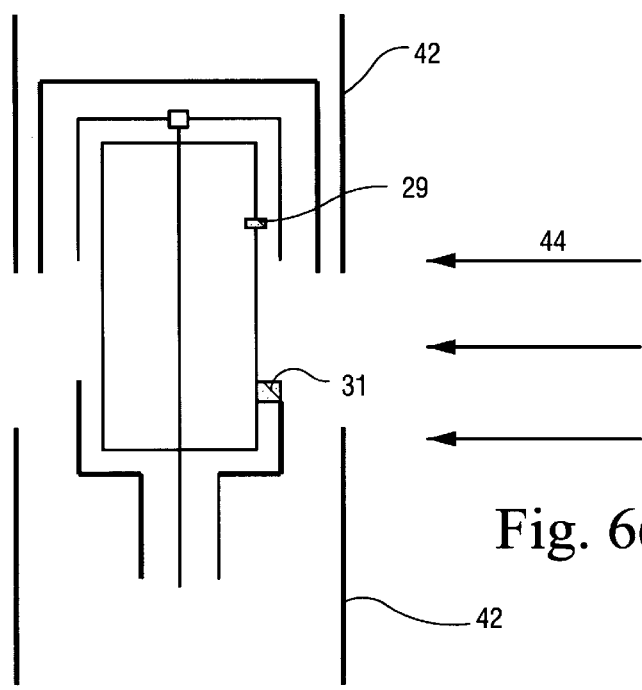

FIGS. 6(a)–(c) illustrate a second method according to the present invention. In FIG. 6(a), cap 26 is provided with platinum outer cap 34 and the two are brazed together at 27 with a first active braze alloy. In FIG. 6(b), the brazed assembly of cap 26 and platinum outer cap 34 are brazed at 29 using a second lower temperature active braze alloy to the ceramic insulator 18, and the adapter 12 is brazed to the insulator at 31 using the same lower temperature active braze alloy. The compositions of the first and second active braze alloys are set forth below:

High Temperature (ABA): 80–90 wt % Ni; 5–8 wt % Cr; 2–4 wt % B; 3–4 wt % Si (Braze Temperature: 980–1040° C.)

Low Temperature (ABA): 58–72 wt % Ag; 26–28 wt % Cu; 2–4 wt % Ti;

(Braze Temperature: 920–960° C.)

The liquidus of the active braze alloy used in the second step is usually at least 60–80° C. lower than the solidus of the active braze alloy employed in the first step.

As an optional third step (FIG. 6(c)), the post cap and adapter are masked with mask 42 and the assembly is plasma sprayed with CSZ, MSZ and/or YSZ powder 44, at an elevated temperature, typically in the region of 500–700° C. The resultant coating covers the insulator and braze joints 29, 31 and provides corrosion protection to the braze joints. In addition, the solid ceramic layer acts as a thermal barrier and provides protection against thermal shock by moderating against any temperature transients which may occur in the surrounding environment. This minimizes the magnitude of thermal shock(s) in the metal to ceramic braze joint(s).

Evaluation of the braze joints for leaks with sensor assemblies fabricated using either of the above-described methods was carried out using standard procedures. The joints passed the standard leak test of less than $10^{-9}$ stdcc/hr He.

Figure 7:
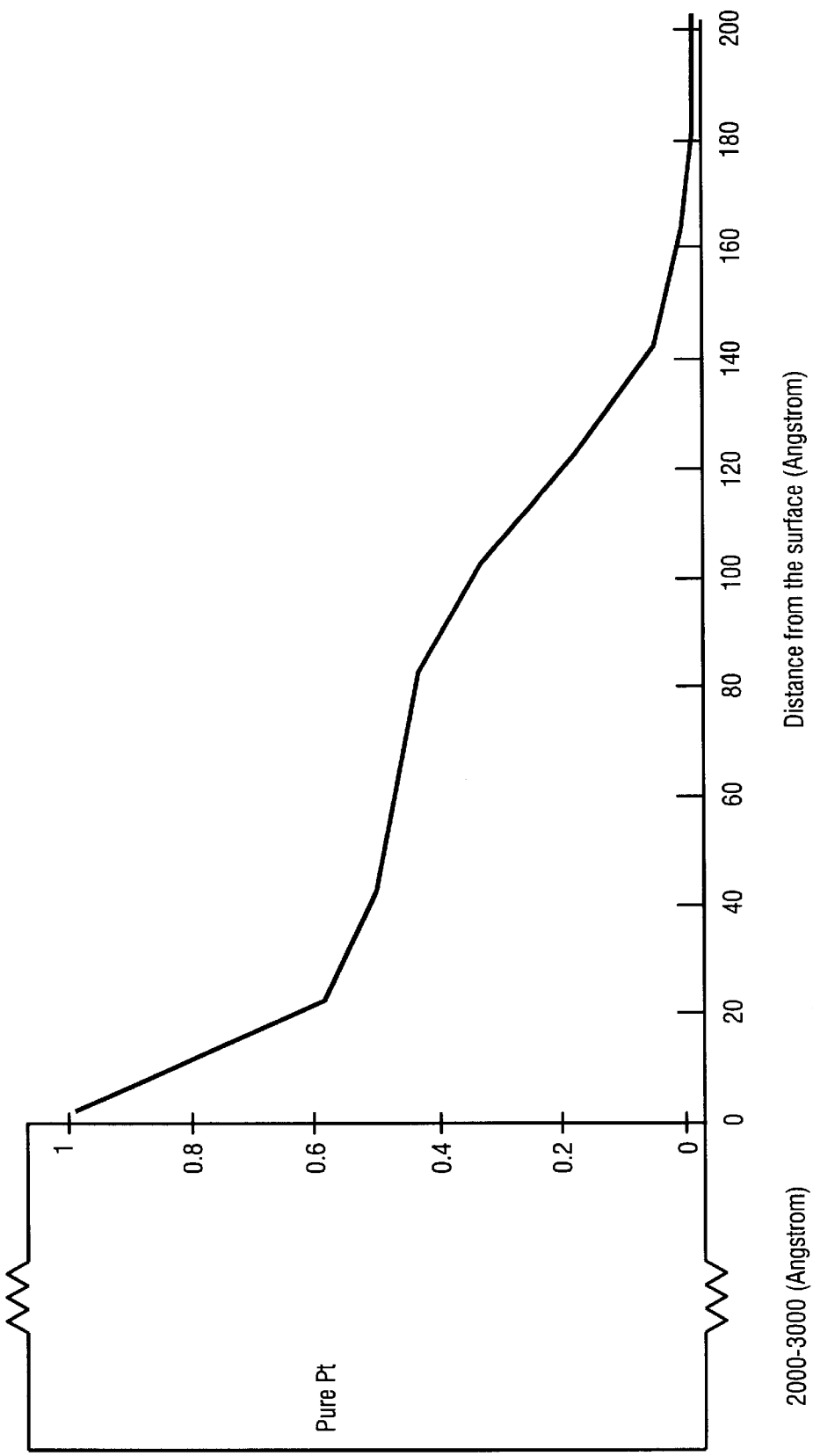
FIG. 7 is a plot showing the expected concentration profile of ion plated Pt on Alloy 42 substrate.

FIG. 7 is a plot of expected concentration profile of ion plated platinum on Alloy 42 substrate. The platinum was deposited by ion implantation technique in order to allow the platinum to diffuse into the surface and form a strong metallic bond with the substrate. This has been qualitatively verified by Auger electron spectroscopy.

The life-span of current platinum ECP sensors is about three to nine months in BWR applications. The sensors produced according to the present invention exhibit extended sensor life to at least one fuel cycle.

The foregoing has been disclosed for the purpose of illustration only. Variations and modifications of the disclosed methods and structures will be readily apparent to practitioners skilled in the art. All such variations and modifications are intended to be encompassed by the claims set forth hereinafter.

What is claimed is:

1. An electrode comprising a housing, a cap and an insulator braze jointed to said cap and housing, said insulator comprising an alloy selected from the group consisting of calcium oxide-stabilized zirconia (CSZ), magnesium oxide-stabilized zirconia (MSZ) and yttrium oxide-stabilized zirconia (YSZ).

2. An electrode according to claim 1, wherein said MSZ, CSZ and YSZ have the following compositions:

MSZ: $ZrO_2$ with 4–8 wt % MgO

CSZ: $ZrO_2$ with 4–8 wt % CaO

YSZ: $ZrO_2$ with 6–10 wt % $Y_2O_3$.

3. An electrode according to claim 1, wherein said cap comprises an inner cap of alloy 42 and an outer platinum cap.

4. An electrode according to claim 1, and further including a coating of MSZ, CSZ or YSZ over an exterior surface of said insulator and covering said braze joints.

5. A method of fabricating an electrode comprising brazing a cap and an adapter to an insulator, said insulator comprising an alloy selected from the group consisting of calcium oxide-stabilized zirconia (CSZ), magnesium oxide-stabilized zirconia (MSZ) and yttrium oxide-stabilized zirconia (YSZ).

6. A method according to claim 1 comprising the farther step of subjecting said cap to platinum ion implantation.

7. A method according to claim 6, wherein said adapter and cap are masked and said insulator is subjected to a plasma spray of a powder selected from the group consisting of calcium oxide-stabilized zirconia (CSZ), magnesium oxide-stabilized zirconia (MSZ) and yttrium oxide-stabilized zirconia (YSZ).

8. A method according to claim 1 wherein said MSZ, CSZ and YSZ have the following compositions:

MSZ: $ZrO_2$ with 4–8 wt % MgO

CSZ: $ZrO_2$ with 4–8 wt % CaO

YSZ: $ZrO_2$ with 6–10 wt % $Y_2O_3$.

9. A method of fabricating an electrode, comprising steps of:
(a) brazing a platinum outer cap to an inner cap with a first metal braze to produce a brazed assembly; and
(b) brazing said brazed assembly to a ceramic insulator using a second lower temperature metal braze, said ceramic insulator comprising an alloy selected from the group consisting of calcium oxide-stabilized zirconia, magnesium oxide-stabilized zirconia and yttrium oxide-stabilized zirconia.

10. A method according to claim 8, wherein said second metal braze has a melting point at least 60–80° C. lower than said first braze alloy.

11. A method according to claim 8, wherein the cap and adapter are masked to form an exposed region which is plasma sprayed with a powder selected from the group consisting of calcium oxide-stabilized zirconia, magnesium oxide-stabilized zirconia and yttrium oxide-stabilized zirconia at a temperature of 500–700° C.

12. A method according to claim 8 wherein said first metal braze has a composition of 80–90 wt % Ni; 5–8 wt % Cr; 2–4 wt % B; and 3–4 wt % Si.

13. A method according to claim 8 wherein said second metal braze has a composition of 58–72 wt % Ag; 26–28 wt % Cu; and 2–4 wt % Ti.

* * * * *